United States Patent [19]

Blatter et al.

[11] Patent Number: 5,360,576
[45] Date of Patent: Nov. 1, 1994

[54] CHIRAL ALKENYLARYL 2,3-EPOXYALKYL ETHERS, AND THE USE THEREOF IN LIQUID-CRYSTALLINE MIXTURES

[75] Inventors: Karsten Blatter, Mainz; Claus Escher, Mühltal, both of Germany; Takamasa Harada, Inzai, Japan; Peter Harnischfeger, Darmstadt; Wolfgang Hemmerling, Sulzbach, both of Germany

[73] Assignee: Hoechst Aktiengesellschaft, Frankfurt am Main, Germany

[21] Appl. No.: 965,366

[22] PCT Filed: Jul. 19, 1991

[86] PCT No.: PCT/EP91/01365
§ 371 Date: Jan. 21, 1993
§ 102(e) Date: Jan. 21, 1993

[87] PCT Pub. No.: WO92/01685
PCT Pub. Date: Jun. 2, 1992

[30] Foreign Application Priority Data

Jul. 20, 1990 [DE] Germany .............. 4023027

[51] Int. Cl.$^5$ .............. C09K 19/34; C07D 405/12; C07D 303/12
[52] U.S. Cl. .............. 252/299.61; 252/299.01; 504/238; 504/239; 504/242; 504/304; 504/336; 549/555; 549/560
[58] Field of Search ........ 252/299.01, 299.61; 544/238, 239, 242, 304, 334, 336, 555, 560; 359/104

[56] References Cited

U.S. PATENT DOCUMENTS

| | | | |
|---|---|---|---|
| 4,876,028 | 10/1989 | Hemmerling et al. | 252/299.61 |
| 4,927,244 | 5/1990 | Bahr et al. | 359/103 |
| 4,973,425 | 11/1990 | Kazuhiko et al. | 252/299.61 |
| 4,988,459 | 1/1991 | Scherowsky et al. | 252/299.61 |
| 5,206,751 | 4/1993 | Escher et al. | 252/299,01 |

FOREIGN PATENT DOCUMENTS 3633968 4/1988 Germany.

OTHER PUBLICATIONS

D. M. Walba et al., Internationale Flüssigkeitsknoferenz, (1986), "Synthesis and Some Properties of a New Class of Ferroelectric and Chiral Nematic Liquid Crystals Containing the 2,3-Epoxy Alcohol Unit".

*Primary Examiner*—Susan Wu
*Attorney, Agent, or Firm*—Curtis Morris & Safford

[57] ABSTRACT

Compounds of the formula (I) in which the symbols have the following meanings: $R^1$ is straight-chain or branched ($C_3$–$C_2$)alkenyl containing a terminal double bond, it being possible for one or two non-adjacent $CH_2$ groups to be replaced by O and/or S atoms, A and B, independently of one another, are phenyl, diazine-2,5-diyl or diazine-3,6-diyl, with the proviso that one of the groups A or B is phenyl and the other is diazine, X is O or S, $R^2$, $R^3$ and $R^4$, independently of one another, are H, straight-chain ($C_1$–$C_{10}$)alkyl or branched ($C_3$–$C_{10}$)alkyl, $R^2$, $R^3$ and $R^4$ not simultaneously being H, have the property of increasing the phase width in CC mixtures or depressing the melting point.

6 Claims, No Drawings

CHIRAL ALKENYLARYL 2,3-EPOXYALKYL ETHERS, AND THE USE THEREOF IN LIQUID-CRYSTALLINE MIXTURES

Particularly in the last decade, liquid crystals have found their way into various industrial areas in which electro-optical and display device properties are required (for example in watch, calculator and typewriter displays). These display devices are based on the dielectric alignment effects in the nematic, cholesteric and/or smectic phases of the liquid-crystalline compounds, the dielectric anisotropy causing the molecular long axis of the compounds to adopt a preferential alignment in an applied electric field. The usual response times in these display devices are rather too long for many other potential areas of application of liquid crystals, which are per se very promising chemical compounds for industry due to their unique properties. This disadvantage is particularly noticeable if, as is necessarily the case in relatively large display element areas, a large number of pixels must be addressed, which would mean the production costs of equipment containing these relatively large areas, such as video equipment, oscillographs or TV, radar, EDP or wordprocessor screens, would be too high.

In addition to nematic and cholesteric liquid crystals, tilted smectic liquid-crystal phases have also been increasing in importance for practical applications for some years. If such tilted smectic phases, in particular smectic C ($S_c$ or SmC) phases are treated with suitable dopes which exhibit or induce in the liquid-crystal phase spontaneous polarization ($P_s$), the phases can be converted into a ferroelectric liquid-crystal phase ($P_s$ specified in $nC.cm^{-2}$); in this respect, see, for example, Lagerwall et al. in the paper "Ferroelectric Liquid Crystals for Displays", SID Symposium, October Meeting, 1985, San Diego (USA). Compared with conventional TN ("twisted nematic") cells, these ferroelectric liquid-crystal phases have response times which are faster by a factor of approximately 1000, so that, also due to other positive properties, such as a possibility of bistable switching, they are good potential candidates for the abovementioned areas of application (for example via matrix addressing).

At the 11th International Liquid-Crystal Conference (30.6. to 4.7.1986) in Berkeley, U.S.A, D. M. Walba presented ferroelectric liquid crystals which contain chiral 2,3-epoxyalkyl side chains and have the following formula:

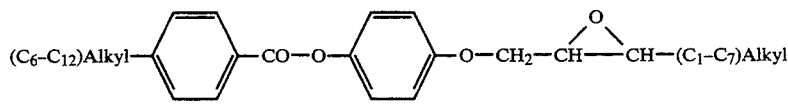

The compound containing a $C_{10}$-alkyl or $C_3$-alkyl radical has an SmC* phase between 75° C. and 80° C.; the response time (75° C., 15 V/ μm) is 14 μsec, and the value for the spontaneous polarization $P_s$ is 45 $nC/cm^2$.

DE-A 36 33 968 describes compounds of the formula (I)

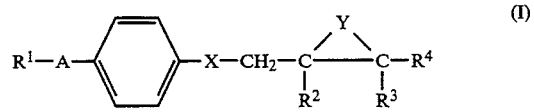

where the symbols have the following meanings:
$R^1$ is straight-chain or branched ($C_1$–$C_{12}$)alkyl, it being possible for one or two non-adjacent $CH_2$ groups to be replaced by O and/or S atoms,
A is diazine-2,5-diyl or diazine-3,6-diyl, X and Y are 0 and/or S, and
$R^2$, $R^3$, and $R^4$, independently of one another, are H, straight-chain ($C_1$–$C_{10}$)alkyl or branched ($C_3$–$C_{10}$)alkyl, $R^2$, $R^3$ and $R^4$ not simultaneously being H.

These compounds induce high spontaneous polarization in liquid-crystalline mixtures.

The object of the present invention is to indicate unsaturated compounds which increase the phase width in LC mixtures and depress the melting point of the mixtures, which have high values for the inherent or spontaneous polarization $P_s$, induced in liquid-crystal phases and contain structural elements which also make them "compatible" (i.e. miscible) with other components in liquid-crystal systems, since, inter alia, the mesogenic part of the molecules is frequently responsible for good "compatibility" with the other mixture components in liquid-crystal systems; these compounds need not necessarily themselves be liquid-crystalline, in particular need not necessarily have an $S_mC$ phase.

The invention proceeds from known chiral compounds containing a mesogenic aromatic unit and a chiral unit containing a heterocyclic three-membered ring.

The compounds according to the invention have the formula

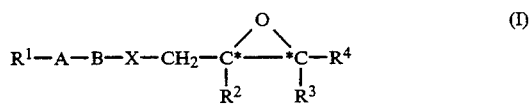

in which the symbols have the following meanings:
$R^1$ is straight-chain or branched ($C_3$–$C_{12}$)alkenyl containing a terminal double bond, it being possible for one or two non-adjacent $CH_2$ groups to be replaced by O and/or S atoms,
A and B, independently of one another, are phenyl, diazine-2,5-diyl or diazine-3,6-diyl, with the proviso that one of the groups A or B is phenyl and the other is diazine,
X is O or S,
$R^2$, $R^3$ and $R^4$, independently of one another, are H, straight-chain ($C_1$–$C_{10}$)alkyl or branched ($C_3$–$C_{10}$)alkyl, $R^2$, $R^3$ and $R^4$ not simultaneously being H.

The N atoms in the diazine ring system may be in the 1,3-position (pyrimidines) or in the 1,2-position (pyridazines).

Of the compounds of the formula (I), preference is given to those in which the symbols have the following meanings: $R^1$ is straight-chain ($C_5$–$C_{11}$)alkenyl, it being possible for one CH₂ group to be replaced by an O or S atom, X is O, $R^2$ and $R^3$ are H and $R^4$ is straight-chain or branched (C₃-C₇)alkyl.

The compounds of the formula (I) can be prepared, for example, by reacting the phenols or thiophenols of the formula (II), (III) or (IV) with the oxiranes of the formula (V) in which Z is H or a nucleofugic group:

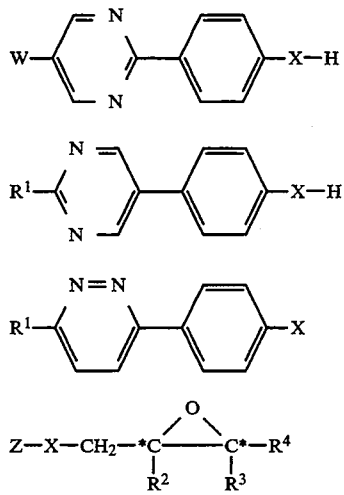

W is $R^1$ benzyloxy tert-butyldimethylsilyloxy or tert-butyldiphenylsilyloxy.

The linking of the mesogenic phenols or thiophenols of the formula (II), (III) or (IV) to the chiral oxiranes of the formula (V) can be effected in a manner known per se, for example by reacting (II), (III) or (IV) with the epoxy alcohols (X=O and Z=H) with the aid of diethyl azodicarboxylate and triphenylphosphine, as described by Mitsonobu, "The Use of Diethyl Azodicarboxylate and Triphenylphosphine in the Synthesis and Transformation of Natural Products" in Synthesis 1981, pp. 1–28. It is also possible to provide the epoxy alcohols with such a nucleofugic group Z that reaction with alkali metal or alkaline earth metal salts of the compounds (II), (III) or (IV) results in the formation of the desired ethers of the formula I (where X=O ). Nucleofugic (leaving) groups of this type which are known to a person skilled in the art include tosylates, brosylates, mesylates and triflates; they can be prepared in a known manner, for example from the alcohols and the respective acid halides.

However, the linking of the mesogen (W=benzyloxy, tert-butyldimethylsilyloxy or tert-butyldiphenylsilyloxy) to the epoxy alcohol can alternatively be carried out as the first step of the synthesis. The benzyl protecting group can be removed by catalytic hydrogenation in THF in the presence of palladium on activated charcoal, and the silyl protecting groups can be removed by treatment with tetrabutylammonium fluoride in THF. In the final step, the phenol formed can be reacted with 1,n-alkenols by the method of Mitsunobu. It is also possible to react the alkali metal or alkaline earth metal salts of this phenol with 1,n-T-alkenes, where T is a nucleofugic group, such as, for example, halide, tosylate, brosylate, mesylate or triflate.

The starting materials are compounds which are known from the literature. For example, the compounds (II) where X=O can be prepared by condensation of substituted benzamides with 2-alkylmalonates, conversion of the resultant dihydroxypyrimidines into dichloropyrimidines and subsequent hydrogenolysis (see DE-C 22 57 588). The compounds (III) where X=O are prepared, for example, by condensation of correspondingly substituted 2-aryl-3-(methylthio)acroleins with suitable amidines [see Kano et al., "A New and Facile Synthesis of 5-arylpyrimidines and 4-arylpyrazoles" in Heterocycles, Vol. 19, No. 6, 1079 to 1082 (1982)]. From the phenols, the corresponding thiophenols are obtained by known methods [for example Newman et al., "The Conversion of phenols to thiophenols via dialkylcarbamates" in J. Org. Chem., 31, pp. 3980–3984 (1966) ].

The oxiranes (epoxy alcohols), as preferred compounds of the formula (V) where X=O and Z=H, are prepared, for example, from the corresponding allyl alcohols by enantio-selective epoxidation (see Pfenninger, "Asymmetric Epoxidation of Allylic Alcohols: The Sharpless Epoxidation" in Synthesis 1986, pp. 89–116). They are then employed as such (Z=H) or alternatively converted into the corresponding tosylates (Z=SO₂C₆H₄CH₃) by sulfonyl methods, for example by reaction with 4-toluenesulfonyl chloride; the same applies to the other nucleofugic groups mentioned.

A further solution to the set object is a twistable liquid-crystal phase containing at least one chiral compound, where the chiral compound is at least one compound of the formula (I). The term "twistable liquid-crystal phase" is taken to mean a nematic, cholesteric or tilted smectic phase, in particular an SmC phase.

The twistable liquid-crystal phases comprise 2 to 20 components, preferably 2 to 15 components, including at least one of the chiral compounds claimed according to the invention. The other constituents are preferably selected from known compounds having nematic cholesteric and/or tilted smectic phases, including, for example, Schiff bases, biphenyls, terphenyls, phenylcyclohexanes, cyclohexylbiphenyls, pyrimidines, esters of cinnamic acid, esters of cholesterol, and various bridged, polycyclic esters of p-alkylbenzoic acids containing terminal polar groups. In general, the commercially available liquid-crystal phases, even before addition of the chiral compound(s), are mixtures of a wide variety of components, of which at least one is mesogenic, i.e. has a liquid-crystal phase [=gives rise to expectations of the formation of at least one enantiotropic (clearing point >melting point) or monotropic (clearing point <melting point) mesophase] as the compound, in derivatized form or in a mixture with certain cocomponents.

In addition to at least one of the chiral compounds claimed according to the invention, the twistable liquid-crystal phase contains, in particular, a phenolpyrimidine compound having an $S_C$ phase, for example a 4-(5-alkylpyrimidin-2-yl)-1-alkoxybenzene.

In liquid-crystalline mixtures, the compounds according to the invention cause, in particular, a reduction in the melting point and a broadening of the temperature range of the smectic phase.

The liquid-crystal mixtures generally contain the compound(s) according to the invention in an amount of from 0.01 to 70% by weight, in particular from 0.05 to 50% by weight.

The compounds according to the invention are particularly suitable as dopes for tilted smectic liquid-crystal phases, since they convert the latter into ferroelectric liquid-crystal phases.

The invention is described in greater detail by means of the Examples below.

EXAMPLES

Example 1

Preparation of:

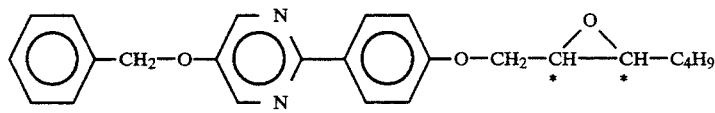

36.72 g (140 mmol) of triphenylphosphine are dissolved in 350 ml of tetrahydrofuran, and 24.38 g (140 mmol=21.77 ml) of diethyl azodicarboxylate are added at 0° C. The mixture is stirred at 0° C. for 20 minutes, the cooling is removed, and 38.96 g (140 mmol) of 5-benzyloxy-2-(4-hydroxyphenyl)pyrimidine in 170 ml of tetrahydrofuran and 18.23 g (140 mmol) of trans-(2S,3S)-3-butyl-2-oxiranemethanol in 140 ml of tetrahydrofuran are added successively to the reaction mixture, which is stirred at room temperature for 48 hours. The mixture is evaporated and the crude product is purified by chromatography on silica gel using dichloromethane/ethyl acetate (15:1). 19.04 g (35%) of a compound of melting point 139.5°–141° C. are obtained.

Example 2

Preparation of:

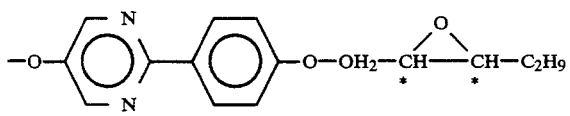

19.0 g (48.8 mmol) of (2S,3S)-3-butyl-2-oxiranemethyl 4-(5-benzyloxypyrimidin-2-yl)phenyl ether in 500 ml of tetrahydrofuran are hydrogenated in a "duck" using hydrogen at atmospheric pressure in the presence of 1.5 g of 10% palladium on activated charcoal and 200 mg of p-toluenesulfonic acid. The reaction solution is filtered through Coriolite, washed with saturated bicarbonate solution and with sodium chloride solution, dried over magnesium sulfate and evaporated. Chromatography on silica gel using dichloromethane/ethyl acetate (4:1) gives 10.89 g of 2-[4-((2S,3S)-3-butyl-2-oxiranemethyloxy)phenyl]-5-hydroxypyrimidine.

Example 3

General working procedure for the preparation of compounds of formula:

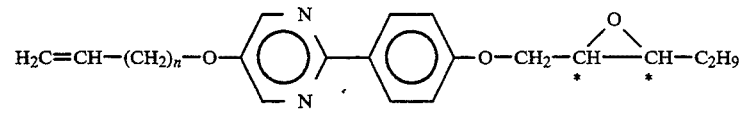

4.97 g (17 mmol) of 2-[4-((2S,3S)-3-butyl-2-oxiranemethyloxy)phenyl]-5-hydroxypyrimidine, 4.64 g (34 mmol) of potassium carbonate and a) 3.58 g (22 mmol) of 6-bromo-1-hexene or b) 4.20 g (22 mmol) of 8-bromo1-octene or c) 4.74 g (22 mmol) of 10-bromo-1-decene or d) 2.66 g (22 mmol) of 3-bromo-1-propene are refluxed for 24–48 hours in 60 ml of methyl ethyl ketone. The solvent is removed, the residue is taken up in 100 ml of chloroform/100 ml of water, the aqueous phase is then extracted with 50 ml of chloroform, and the combined organic phases are washed with water and dried over magnesium sulfate. The solvent is removed, and the residue is recrystallized twice from hot ethanol.

The following are obtained:
a) 3.93 g (60.3%) of 5-(1-hexen-6-yl)oxy-2-[4-((2S,3S)-3-butyl-2-oxiranemethyloxy)phenyl]pyrimidine (1)
b) 4.12 g (60%) of 5-(1-octen-8-yl)oxy-2-[4-((2S,3S)-3-butyl-2-oxiranemethyloxy)phenyl]pyrimidine (2)
c) 4.53 g (62.3%) of 5-(1-decen-10-yl)oxy-2-[4-((2S,3S) -3-butyl-2-oxiranemethyloxy)phenyl]-pyrimidine (3)
d) 3.25 g (56.3%) of 5-(2-propen-3-yl)oxy-2-[4-((2S,3S) -3-butyl-2-oxiranemethyloxy)phenyl]-pyrimidine (4)

Phase sequences:
1: X 78N* 85 I
2: X 73 $S_c$* 85 $S_A$* 89 I
3: X 59 $S_c$* 96 $S_A$* 96 I
4: X 93 I

Use Example

A. A mixture is prepared from the following 6 components (in mol%)

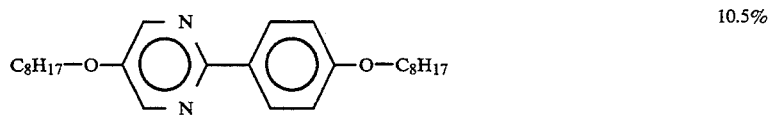

10.5%

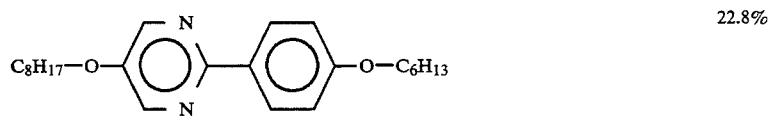

22.8%

-continued

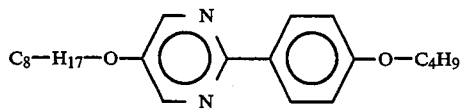  24.1%

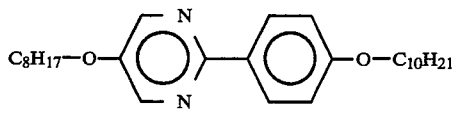  19.1%

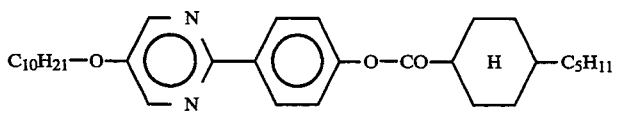  13.5%

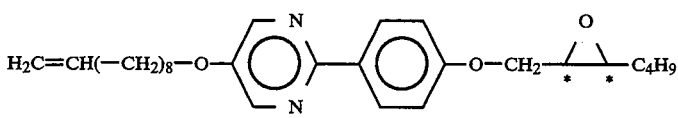  10%

The polarization and response time are then measured at a temperature of 25° C.:

$P_s = 9\ \mu C/cm^2$ $t_s = 200\ \mu s$

The mixture is switchable in a temperature range of from 20° C. to 7° C.

The values for the spontaneous polarization were determined by the method of H. Diamant et al., Rev. Sci. Instr. 28, 30, 1957 (2-μm measurement cell, rubbed polyimide). The response time was determined as in DE-A-39 09 355.

B. The two examples below show the advantageous use of the compounds according to the invention compared with analogous compounds containing fully hydrogenated side chains.

The advantage is in the comparatively high response speed or equivalently in the lower voltage necessary for switching at the same response speed. This is in some cases attributable to a smaller induced switching angle and in some cases to a lower viscosity.

Example
(According to the Invention)

a) 1.92%  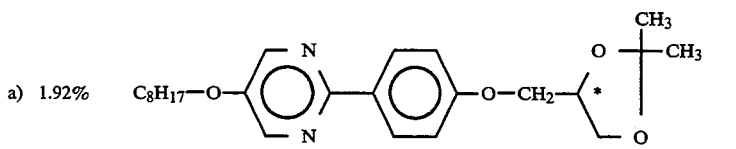  S 3.66%  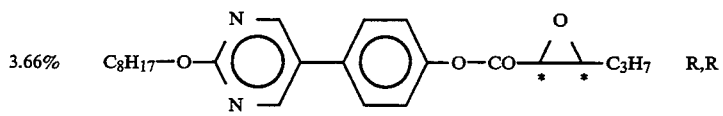  R,R 3.65%  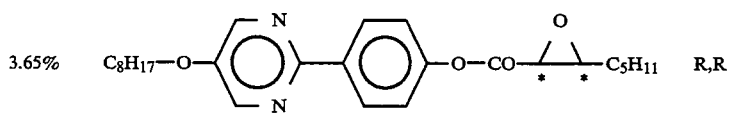  R,R 20.71%  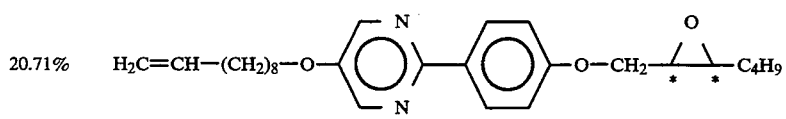

7.53%  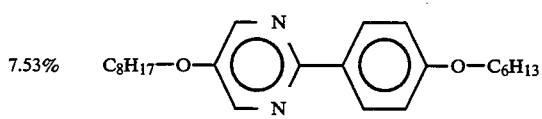

3.48%  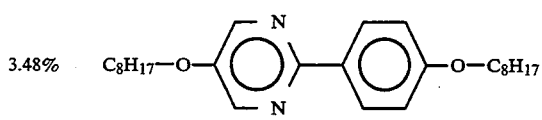

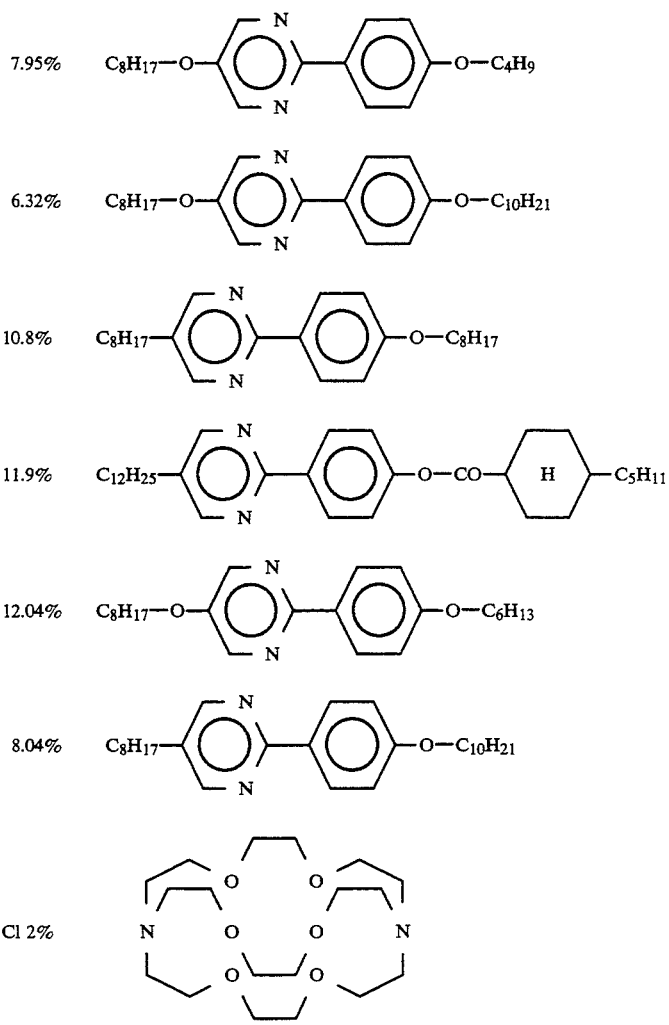
$S_C^*$ 56° $S_A^*$ 75° N 84° I
Ps = 35 nCb/cm²
This mixture has a switching angle of 36.5° and can be brought into the desired switching state by means of a bipolar electrical pulse having a width of 50 μs and a height of 10.4 V/μm.
Comparative Example
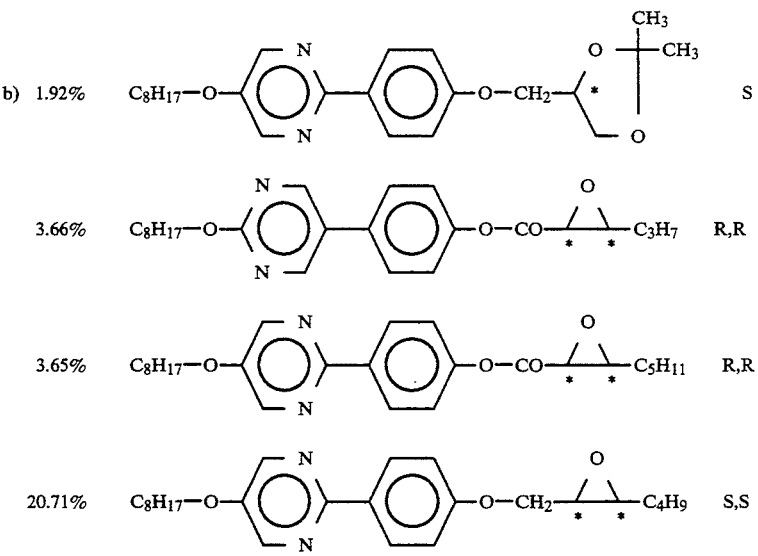

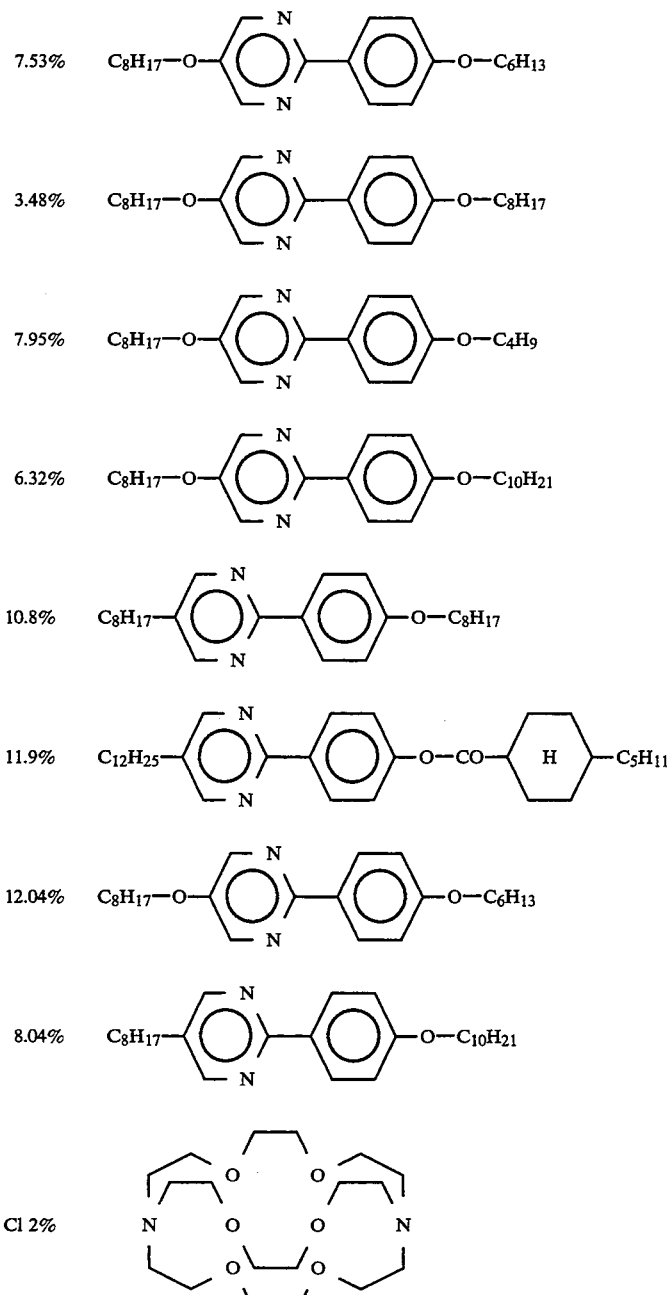

$S_C^*$ 59° $S_A^*$ 70° N 85° I
Ps = 44 nCb/cm²

This mixture has a switching angle of 42.5° and can be brought into the desired switching state by means of a bipolar electrical pulse having a width of 50 μs and a height of 19.6 V/μm.

We claim:

1. A chiral compound containing a mesogenic aromatic unit, an alkene group and a chiral unit containing a heterocyclic three-membered ring, wherein, in the formula (I)

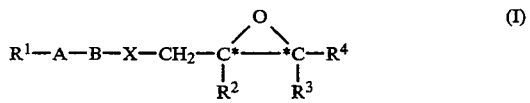

the symbols have the following meanings:

$R^1$ is straight-chain or branched ($C_3$–$C_{12}$)alkenyl containing a terminal double bond, it being possible for one or two non-adjacent $CH_2$ groups to be replaced by O and/or S atoms, A and B, independently of one another, are 1,4-phenylene, diazine-2,5-diyl or diazine-3,6-diyl, with the proviso that one of the groups A or B is phenyl and the other is diazine, X is O or S, and $R^2$, $R^3$ and $R^4$, independently of one another, are straight-chain ($C_1$–$C_{10}$)alkyl or branched ($C_3$–$C_{10}$)alkyl, $R^2$, $R^3$ and $R^4$ not simultaneously being H.

2. A chiral compound as claimed in claim 1, wherein, in the formula (I), the symbols have the following meanings: $R^1$ is straight-chain ($C_5$–$C_{11}$)alkenyl, it being possible for one $CH_2$ group to be replaced by an O or S atom, X is O, $R^2$ and $R^3$ are H and $R^4$ is straight-chain or branched ($C_3$–$C_7$)alkyl.

3. A chiral compound as claimed in claim 1 or 2, wherein A is pyrimidine-2,5-diyl.

4. A twistable liquid-crystal phase containing at least one chiral compound, wherein it contains at least one chiral compound of the formula (I) as claimed in claim 1.

5. A twistable liquid-crystal phase as claimed in claim 4, which contains, in addition to at least one chiral compound of the formula (I) as claimed in claim 1, a phenylpyrimidine compound having an $S_c$ phase.

6. A liquid-crystal display element containing a liquid-crystal phase as claimed in claim 4.

* * * * *